(12) United States Patent
Anderson et al.

(10) Patent No.: US 6,778,851 B2
(45) Date of Patent: Aug. 17, 2004

(54) SYSTEM FOR DETERMINING THE CONDITION OF A PATIENT'S HEART

(76) Inventors: John McCune Anderson, 16 Torgrange, Hollywood, County Down (IE); James Allen, 10 Dunadry Road, Muckamore, County Antrim (IE)

(*) Notice: Subject to any disclaimer, the term of this patent is extended or adjusted under 35 U.S.C. 154(b) by 251 days.

(21) Appl. No.: 09/877,350

(22) Filed: Jun. 8, 2001

(65) Prior Publication Data

US 2002/0055683 A1 May 9, 2002

(51) Int. Cl.$^7$ .............................. A61B 5/0402
(52) U.S. Cl. ........................................ 600/509
(58) Field of Search .................. 600/508, 509, 600/512, 513, 515–518

(56) References Cited

U.S. PATENT DOCUMENTS

| | | | |
|---|---|---|---|
| 4,751,928 A | * 6/1988 | Hallon et al. | 600/508 |
| 5,054,496 A | * 10/1991 | Wen et al. | 600/509 |
| 5,419,337 A | * 5/1995 | Dempsey et al. | 600/515 |
| 5,724,983 A | 3/1998 | Selker et al. | 128/696 |
| 5,792,066 A | * 8/1998 | Kwong | 600/517 |
| 6,217,525 B1 | * 4/2001 | Medema et al. | 600/508 |

FOREIGN PATENT DOCUMENTS

| | | | |
|---|---|---|---|
| EP | 0853 285 A1 | 7/1998 | G06F/17/00 |
| EP | PCT/EP/98/01446 | 9/1998 | A61B/5/04 |

OTHER PUBLICATIONS

Pipberger et al; First and Second Generation Computer Programs for Diagnostic ECG and VCG Classification, Proceedings of the XIIth International Colloquium Vectorcardiographicum, Brussels, Eds. P. Rijlant et al, Presses Academiques Europennes, (cont.) pp. 431–439, 1972.*

Matthes et al, Interaction Analysis of Statical ECG Diagnosis on an Intelligent Electrocardiograph—an Expert Systems Approach, In: Proc. of the Working Conference Computer ECG Analysis—Toward Standardization, Eds. Willems, van Bemmel, (cont), Zywietz, North Holland, pp. 215–220, 1996.*

Goettsch, G., et al.—Extension of the Hanover HES ECG Diagnostic Program Module, Proceedings of the Computers in Cartiology Meeting, US, Washington, IEEE Comp. Soc. Press, vol. Meeting 14, 1987, pp. 151–154, XP000092866.

* cited by examiner

Primary Examiner—Angela D. Sykes
Assistant Examiner—Joseph S Machuga
(74) Attorney, Agent, or Firm—Pillsbury Winthrop LLP

(57) ABSTRACT

A system for determining the condition of a patient's heart comprises a plurality of electrodes for producing cardiac signals and means for converting the cardiac signals into digital form. Data processing means is programmed to process the digital cardiac signals to determine a plurality of parameters of the patient's heartbeat and determine the condition of the patient's heart using a binary decision tree algorithm. The algorithm has a plurality of decision nodes each of which makes a decision based upon the value(s) of a subset of the parameters, the decision criterion of at least one of the said decision nodes being modified according to the value of at least one parameter not of the subset. In addition, at at least one node, the respective subset of parameters may be determined according to the value of at least one parameter not of the subset.

10 Claims, 3 Drawing Sheets

SYSTEM FOR DETERMINING THE CONDITION OF A PATIENT'S HEART

This application claims foreign priority benefits under 35 U.S.C. § 120 and § 365(c) to PCT International Application No. PCT/IB99/02033, filed on Dec. 9, 1999, designating the United States, and which claims priority to Irish Patent Application No. S981036, filed on Dec. 9, 1998.

FIELD OF THE INVENTION

This invention relates to a system for determining the condition of a patient's heart.

BACKGROUND OF THE INVENTION

The use of electrocardiographic (ECG) information to detect ischaemic heart disease (IHD) is not new. The standard twelve lead ECG has been used by clinicians for decades for early detection of ischaemic events. The procedure involves the use of 10 appropriately placed electrodes and suitable instrumentation amplifiers to acquire 12 separate ECG signals. These signals are then interpreted either visually or by automated software to identify ischaemic signs. Unfortunately, the area of the torso covered by these 10 electrodes is insufficient to detect ischaemic events from all areas of the heart. This means that the standard twelve lead ECG in many instances fails to provide unequivocal diagnosis.

An improved method is the use of unipolar body surface mapping (BSM) which uses a multitude of electrodes (typically between 32 and 200 electrodes) distributed across both the anterior and posterior surface of the torso. With such a system the amount of information being presented to the user is impractical. Furthermore, with large numbers of electrodes, the system requires a significant amount of time to be applied to the patient. One approach of particular interest is by Lux et al. "Redundancy reduction for improved display and analysis of Body Surface Potential Maps I spatial compression", Circulation Res, Vol. 49, 186–196; where a Karhunen-Loeve method is described which allows a minimal lead set to be recorded and then later expanded mathematically to a more detailed lead set.

Investigations concerning the analysis of such BSM's both directly recorded and expanded mathematically has resulted in various different analysis techniques. All of these however are essentially enhancements to the analysis techniques used to interpret the standard 12 Lead ECG. BSM information is unique in that it provides an overall body surface electrical pattern. This pattern is distinctive and must be analyzed in a way which takes advantage of the information contained within it.

The use of vectors in ECG interpretation is known, the most famous being Vectorcardiographic systems which are no longer common. All of these vector analysis techniques however concentrate upon the discrete amplitude of the vector drawn between a maximum and a minimum point of electrical potential. One such system is disclosed in European Patent Specification EP-A-0512 719 B1 where a system is described for detecting coronary artery disease by use of a discriminant function. Here one such parameter which could be analyzed is the overall QRST vector. This would be a vector drawn between the maximum and the minimum point of a QRST isointegral BSM.

The use of discriminant functions as described above has been for many years arguably the best method for analyzing the parameters and features extracted from BSM's. One notorious problem with a discriminant function approach is the lack of determinism associated with such a technique. Given any particular case or set of parameters it is very difficult to see what output a given function will provide and given an output it is very difficult to determine how the function arrived at that decision.

The use of a more conventional decision tree approach has not been considered appropriate since the problem possesses so many dimensions. Having obtained a decision node (using binary comparison of a given parameter to a preset threshold), which will reliably and accurately detect one given patient condition, it is later found that the same decision fails when complicated by other real life conditions. For example, having devised a decision tree which can be useful in detecting acute myocardial infarction occurring in all areas of the myocardium, this same algorithm then fails when there are two areas of the myocardium infarcting at the same time, when the heart is abnormally shaped due for instance to hypertrophy or when the infarct is complicated by a disorder of the conduction system.

SUMMARY OF THE INVENTION

It is an object of the present invention to provide a means for analyzing cardiac information which can provide an improved diagnostic capability with a clearly traceable path to the resulting decision.

Accordingly, the invention provides a system for determining the condition of a patient's heart, comprising:
(a) a plurality of electrodes each capable of detecting the electrical activity associated with a heartbeat of the patient and producing a corresponding cardiac signal,
(b) means for converting the cardiac signals into digital form, and
(c) data processing means programmed to:
  (1) process the digital cardiac signals to determine a plurality of parameters of the patient's heartbeat,
  (2) determine the condition of the patient's heart using a binary decision tree algorithm, such algorithm having a plurality of decision nodes each of which makes a decision based upon the value(s) of a respective subset of the parameters, the decision criterion of at least one of the said decision nodes being modified according to the value of at least one parameter not of the respective subset, and
  (3) provide an output indicative of the condition of the patient's heart so determined.

BRIEF DESCRIPTION OF THE DRAWINGS

Embodiments of the invention will now be described, by way of example, with reference to the accompanying drawings, in which.

DETAILED DESCRIPTION OF THE INVENTION

Figure 1:
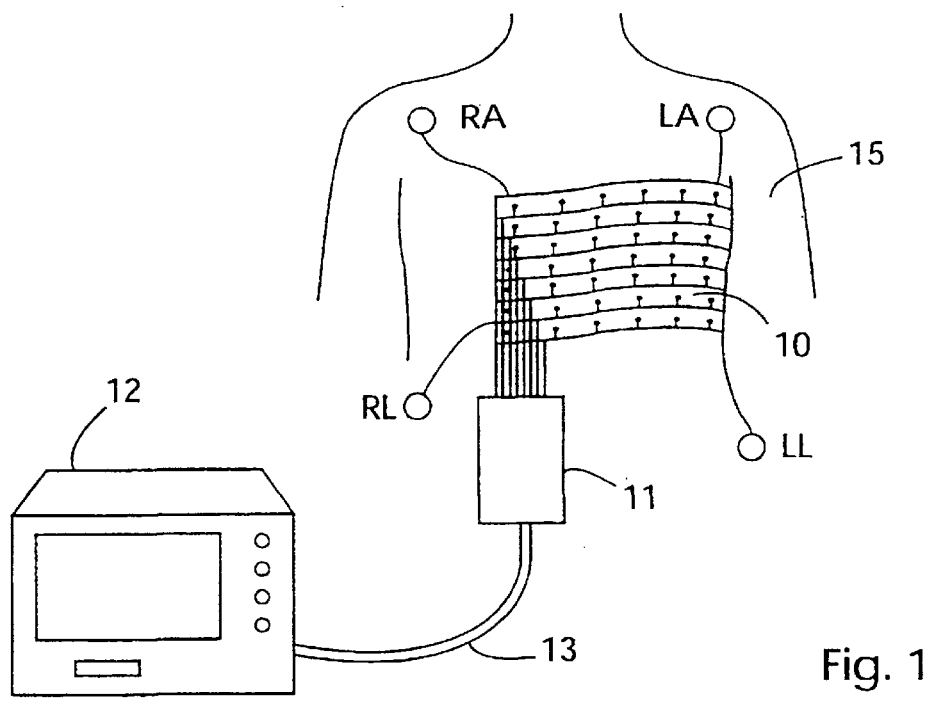
FIG. 1 is a schematic view of a system according to one embodiment.

Referring to FIGS. 1–4, in one embodiment a system according to the invention includes a two-dimensional array 10 of a plurality of ECG electrodes removably attachable to a human patient's torso 15. As shown in FIG. 1 the electrodes are attached to the anterior surface of the torso but they can extend substantially fully around the torso. The number of electrodes in the array can typically vary from 20 to 100; in the present case it is assumed there are 96 electrodes. The array 10 also includes right arm (RA), left arm (LA), right leg (RL), and left leg (LL) electrodes and may be constructed as described in International Application Number PCT/1B95/01043 (WO96/14015).

Each electrode is capable of detecting the electrical activity associated with the patient's heartbeat and producing a corresponding cardiac signal, and it will be appreciated that each electrode in the array 10, although detecting the same activation of the heartbeat at any given instant, receives the signal with a different voltage having regard to its different spatial position relative to the heart. Since the electrode signal typically has a strength in millivolts it requires amplification prior to further processing. This is achieved in an interface unit 11 which performs front end amplification and analogue-to-digital (A/D) data conversion. The unit 11 may be constructed as described with reference to FIG. 4 of International Application Number PCT/IB97/01631 (W098/26712).

Briefly, however, the total set of 96 signals from the array 10 is divided into six channels of 16 signals per channel. Each channel contains 16 banks of amplification, filtering and sample/hold devices, and a respective 16-to-1 analogue signal multiplexer in each channel is used to sequentially switch through each of the 16 signals during each sample/hold period to enable a single channel digital conversion to be used. A microcontroller controls the process of freezing the 16 analogue signals in each channel and during each sample/hold period the analogue multiplexer is selected 16 times with each step sequentially switching one of the 16 signals through to an A/D converter. The sampling frequency is at least 500 Hz and preferably at least 1 khz.

The interface unit 11, therefore, produces successive sets of 96 sampled and analogue to digital converted signal values, each set having been derived during a respective sample/hold period and therefore constituting a "snapshot" of the electrode voltages at the respective sampling instant. With a sampling frequency of 1 KHz, 1000 sets of 96 signals will be produced per second.

Figure 2:
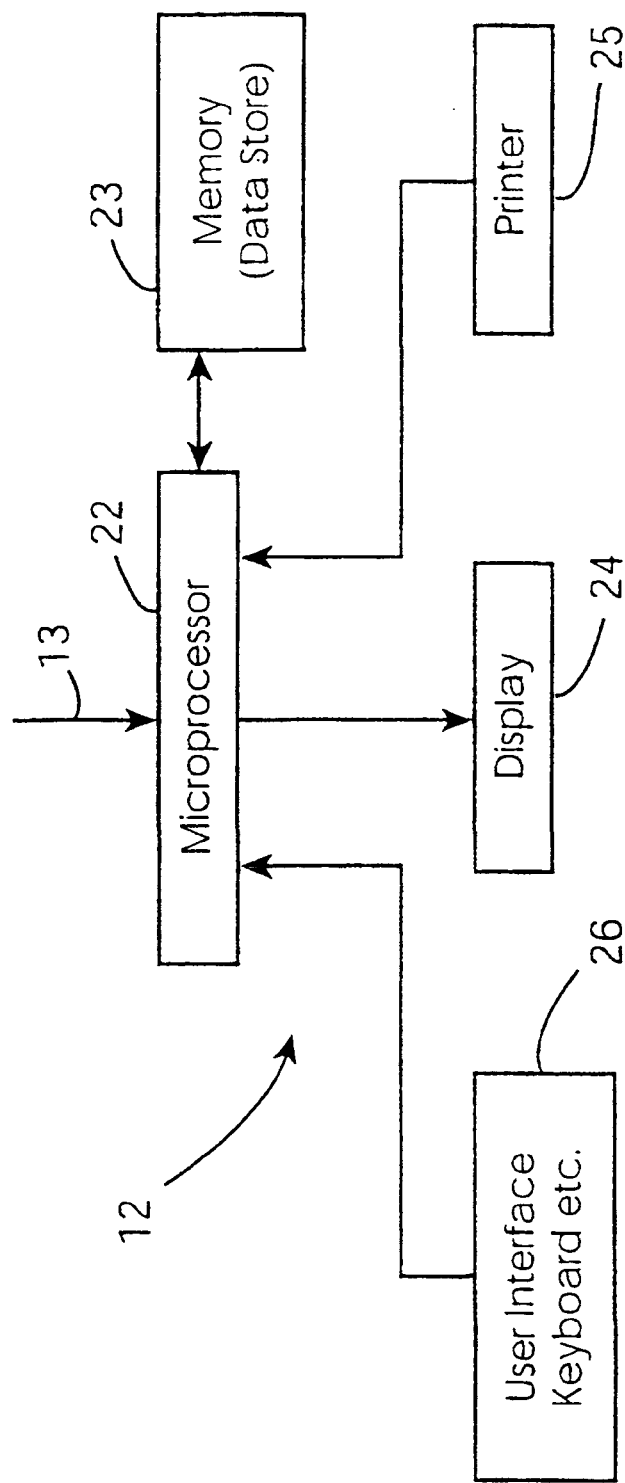
FIG. 2 is a block diagram of the storage, processing and display unit of FIG. 1.

The digitized cardiac signals are passed via a direct digital link 13 to a storage, processing and display unit 12, FIG. 2, comprising a microprocessor 22, a storage device 23, an electronic display device, such as a CRT monitor 24, a printer 25 and a user interface, such as a keyboard 26. The microprocessor 22 polls each of the channels to transfer sampled data into the storage device 23. In particular, once patient hook-up is satisfactorily completed, the microprocessor 22 stores a pre-selected time frame (typically 5 seconds) of all the channels into the storage device 22. The microprocessor 22 is programmed to process the stored digital data according to the flowchart shown in FIG. 3.

First (Step 100,) the program extracts certain parameters from the digital signals. In the present embodiment these are QRS Integral, ST-T Integral, ST0ms Isopotential, ST60 ms Isopotential, ST100 ms Isopotential and $V_{Symmetry}$. Apart from $V_{Symmetry}$, these parameters are well known in the art and methods for their extraction are also well known.

The parameter $V_{Symmetry}$ is given by:

$$V_{Symmetry} = V_{Max} - V_{Min}$$

where $V_{Max}$ is the maximum ST60 ms isopotential static vector and $V_{Min}$ is the minimum ST60 ms isopotential static vector, ST60 ms isopotential being defined as the isopotential map constructed from all electrode locations at the time instant 60 milliseconds after the 'J' point in the ECG cycle. These vectors are described in International Application Number PCT/EP98/01446 (WO 98/4 0010).

Figure 4:
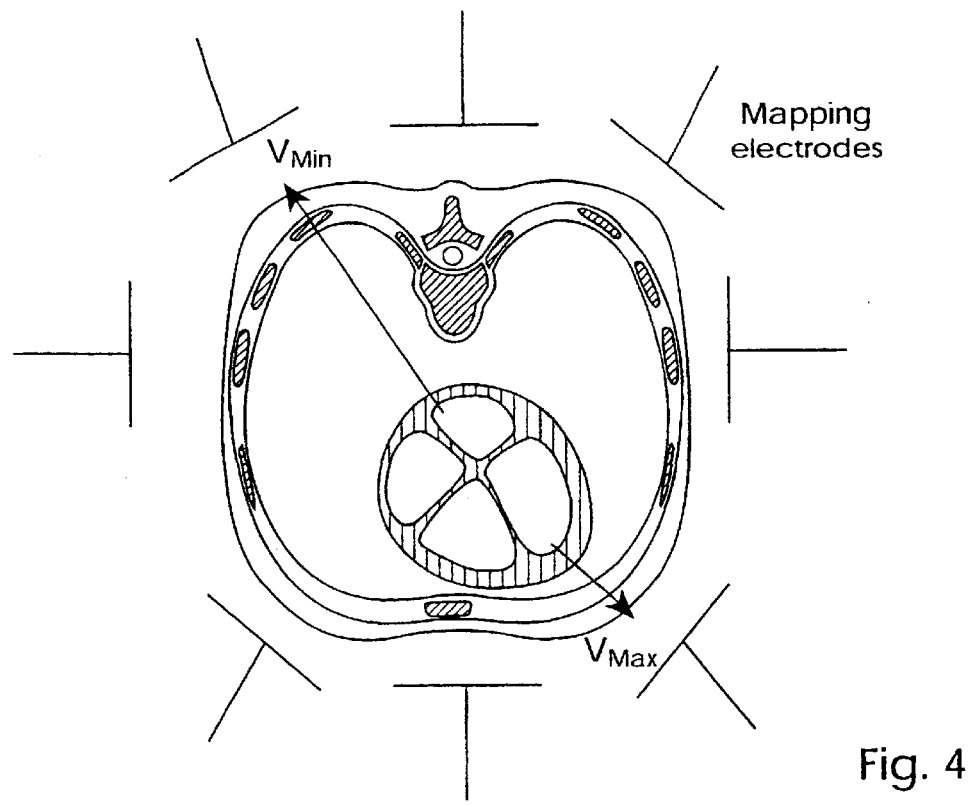
FIG. 4 is an example of spatial resultant vectors (static vectors) measured on the body surface with reference to the Wilson Central Terminal (WCT).

Referring to FIG. 4, it can be seen that the $V_{Max}$ vector is the vector drawn from the WCT to the overall maximum location on the body surface and $V_{Min}$ is the vector drawn from the WCT to the overall minimum location. The length shown in FIG. 4 is for demonstration only and in reality does not reflect the distance between the WCT and the body surface, but rather the magnitude of the electrical signal detected on the body surface. The vectors are referred to as "static" to denote that the vectors are either snapshots or averages of dynamically changing information.

Having extracted these parameters, the program implements a binary decision tree algorithm comprising, in one embodiment, six binary decision nodes 102 to 112 which test as follows:

| Node 102 | Ischaemic/Normal? |
| Node 104 | Normal/Abnormal Conduction? |
| Node 106 | AMI (Acute Myocardial Infarction) with Conduction Disorder? |
| Node 108 | Classic AMI? |
| Node 110 | AMI with LVH (Left Ventricular Hypertrophy)? |
| Node 112 | AMI with ST Depression? |

Figure 3:
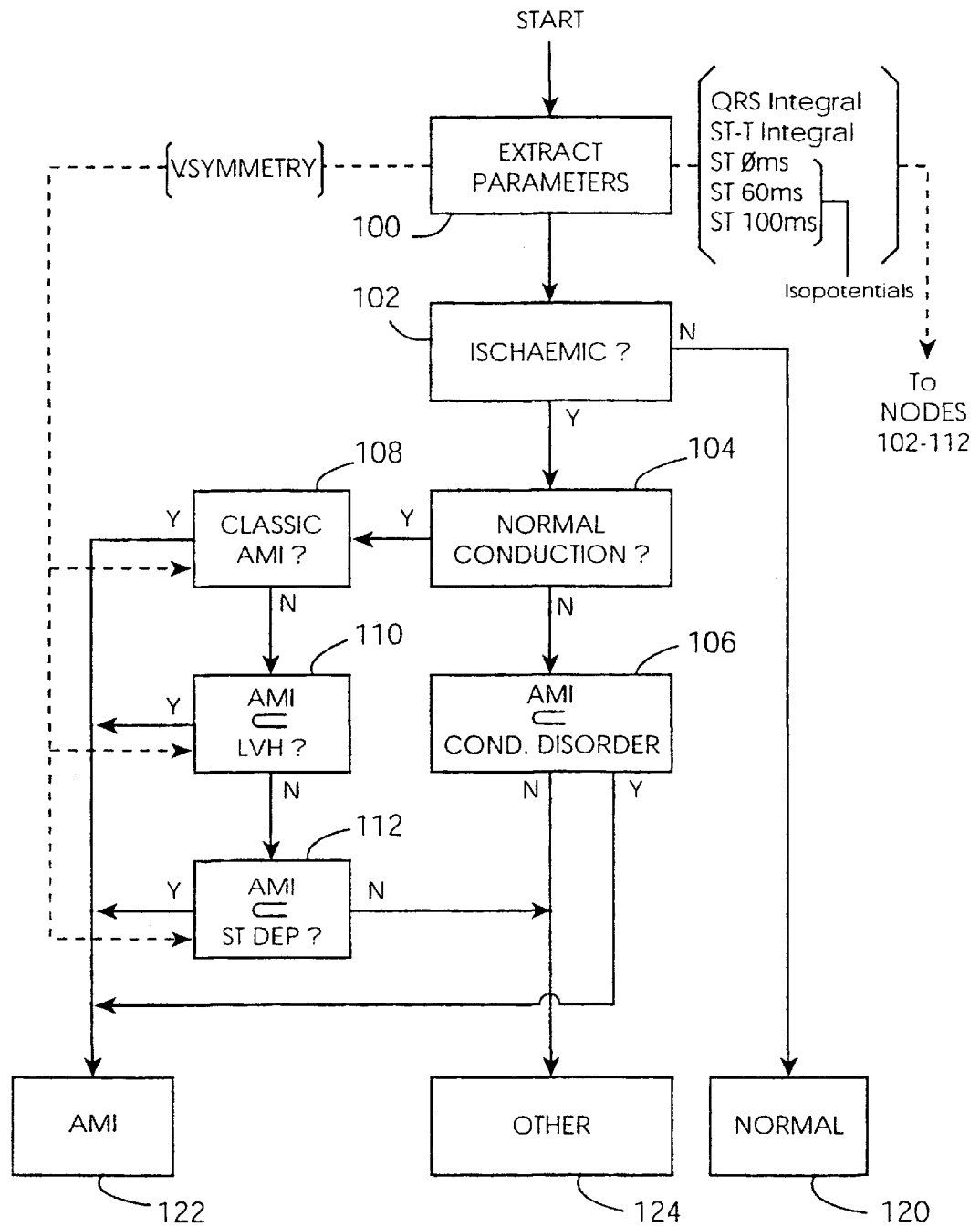
FIG. 3 is a flowchart of the program stored in the unit of FIG. 2.

As indicated by the dashed line on the RHS of FIG. 3, at each node 102–112 the respective test is made on the basis of the value(s) of one or more of the parameters QRS Integral, ST-T Integral, ST0ms Isopotential, ST60ms Isopotential and ST100ms Isopotential, the relevant parameter (s) being compared with respective threshold(s) associated with the node to determine the binary outcome, yes (Y) or no (N), of the node. For example, node 108 tests to see if both ST0ms Isopotential and ST60 ms Isopotential are above certain respective thresholds, node 110 tests to see if both ST60 ms Isopotential and ST-T Integral are below certain respective thresholds, while node 112 tests to see if both ST0ms Isopotential and ST60 ms Isopotential are below certain respective thresholds. The nature of the tests made at the nodes 102–112 will be known to those skilled in the art.

By following through the logic of the flowchart, it will be seen that, depending upon the decisions at the nodes, the program will output "Normal" (Step 120) indicating that the heart is normal, "AMI" (Step 122) indicating Acute Myocardial Infarction or "Other" (Step 124) indicating some other abnormality. The output is displayed in human-readable form on the CRT monitor 24, FIG. 2, or may be printed out or otherwise displayed.

In order to improve the accuracy of the diagnosis, the static vector symmetry, which changes depending upon the condition of the heart, is used to adaptively control the thresholds used by the decision algorithm. Thus, in the present embodiment and as indicated by the dashed line on the LHS of FIG. 3, the parameter thresholds associated with each of the nodes 108, 110 and 112 are varied according to the magnitude of $V_{Symmetry}$. This may be achieved by storing, e.g. in a look-up-table, a number of different thresholds for each parameter ST-T Integral, ST0ms Isopotential and/or ST60 ms Isopotential tested by the node and selecting a particular one of the thresholds according to the magnitude of $V_{Symmetry}$.

In a simple case there will be two thresholds stored for each parameter tested by a node, and one or other will be selected according to whether $V_{Symmetry}$ is itself above or below a certain threshold (i.e. above or below a certain symmetry level). However, since $V_{Symmetry}$ is a continuously variable parameter, the nodes could use a function $f(V_{Symmetry})$ to select the parameter threshold.

It should be noted that unlike a discriminant function or an artificial neural network (ANN) which are probalistic, the adaptive algorithm described above is deterministic in that for any given case it is easy to determine how the algorithm will perform and also that given an output it is very easy to determine how the algorithm arrived at its decision.

The above is given only as an example of the invention, and modifications are possible. For example, the binary decision tree algorithm may be more or less complex than that shown, and may use more or less, and/or different, parameters in its operation. Thus, the $V_{Max}$ and $V_{Min}$ vectors used to derive $V_{Symmetry}$ are only given by way of example since similar vectors usable in the invention can be constructed from QRS isointegral maps, STT isointegral maps, as well as ST0ms isopotential and ST100 ms isopotential maps. Also, although only one parameter, $V_{Symmetry}$ has been used to adaptively control certain of the decision nodes, in general, and depending on the complexity of the binary decision tree algorithm, more than one parameter can be used to adaptively control the nodes. This may include using more than one parameter to adaptively control an individual node or using different parameters to adaptively control different nodes.

In addition, one or more parameters may be used to determine which of the other parameters are used at a decision node. For example, in FIG. 3, node 110 may use the parameters ST-T Integral and ST60 ms Isopotential if $V_{Symmetry}$ is below a certain value and use the parameters ST-T Integral and ST0ms Isopotential if $V_{Symmetry}$ is above that value.

Furthermore, the decision thresholds for the chosen parameters may themselves be varied according to the value of another parameter. For example, in the case above, the value of $V_{Symmetry}$ is used to select which two out of three parameters to use at, decision node 110. The value of the QRS integral may then be used to determine the decision thresholds to apply to those selected parameters.

Having thus described at least one illustrative embodiment of the invention, various alterations, modifications and improvements will readily occur to those skilled in the art. Such alterations, modifications and improvements are intended to be within the scope and spirit of the invention. Accordingly, the foregoing description is by way of example only and is not intended as limiting. The invention's limit is defined only in the following claims and the equivalents thereto.

What is claimed is:

1. A system for determining the condition of a patient's heart, comprising:
   (a) a plurality of electrodes, each electrode capable of detecting the electrical activity associated with a heartbeat of a patient and producing a corresponding cardiac signal,
   (b) means for converting the cardiac signals into digital form, and
   (c) data processing means programmed to:
       (1) process the digital cardiac signals to determine a plurality of parameters of the patient's heartbeat,
       (2) determine the condition of the patient's heart using a binary decision tree algorithm, such algorithm having a plurality of decision nodes each of which makes a decision based upon the value(s) of a respective subset of the parameters, the decision criterion of at least one of the said decision nodes being modified according to a measured value of at least one parameter not of the respective subset, and
       (3) provide an output indicative of the condition of the patient's heart so determined.

2. The system of claim 1, wherein at each node the decision is made according to whether or not the value(s) exceed respective threshold(s), the threshold(s) being varied according to the measured value of the said at least one parameter not of the subset.

3. The system of claim 2, wherein the threshold(s) are varied according to whether or not the measured value of the said at least one parameter not of the subset exceeds a certain threshold.

4. The system of claim 3, wherein at at least one node the respective subset of parameters is determined according to the measured value of at least one parameter not of the subset.

5. A system for determining the condition of a patient's heart, comprising:
   (a) a plurality of electrodes, each electrode capable of detecting the electrical activity associated with a heartbeat of a patient and producing a corresponding cardiac signal,
   (b) means for converting the cardiac signals into digital form, and
   (c) data processing means programmed to:
       (1) process the digital cardiac signals to determine a plurality of parameters of the patient's heartbeat.
       (2) determine the condition of the patient's heart using a binary decision tree algorithm, such algorithm having a plurality of decision nodes each of which makes a decision based upon the value(s) of a respective subset of the parameter, the decision criterion of at least one of the said decision nodes being modified according to a measured value of at least one parameter not of the respective subset wherein the measured value is determined by $V_{Max}-V_{Min}$ where $V_{Max}$ is the maximum isopotential static vector taken at a predetermined time instant in the ECG cycle and $V_{Min}$ is the minimum ispotential static vector taken at substantially the same time instant in the ECG cycle, and
       (3) provide an output indicative of the condition of the patient's heart so determined.

6. The system of claim 5, wherein the time instant is 60 milliseconds after the 'J' point.

7. The system of claim 5, wherein the time instant is the 'J' point.

8. The system of claim 5, wherein at each node the decision is made according to whether or not the value(s) exceed respective threshold(s), the threshold(s) being varied according to the measured value.

9. The system of claim 8, wherein the threshold(s) are varied according to whether or not the measured value exceeds a certain threshold.

10. The system of claim 9, wherein at at least one node the respective subset of parameters is determined according to the measured value.

* * * * *

UNITED STATES PATENT AND TRADEMARK OFFICE
CERTIFICATE OF CORRECTION

PATENT NO. : 6,778,851 B2
DATED : August 17, 2004
INVENTOR(S) : John M. Anderson et al.

It is certified that error appears in the above-identified patent and that said Letters Patent is hereby corrected as shown below:

Title page,
Item [76], Inventors, replace "Hollywood, County Down (IE)" with -- Holywood, County Down (IE) --.
Item [30], Foreign Application Priority Data, should read
-- December 9, 1999 PCT/IB99/02033 John M. Anderson et al. --.

Column 1,
Line 4, replace "claims foreign priority benefits under 35 U.S.C. § 120 and §365(c)" with -- is a continuation of --.

Signed and Sealed this

Fourth Day of January, 2005

JON W. DUDAS
*Director of the United States Patent and Trademark Office*